United States Patent [19]
Cooney, Jr. et al.

[11] Patent Number: 5,905,037
[45] Date of Patent: *May 18, 1999

[54] LIQUID SEPTIC TANK TREATMENT COMPOSITION

[75] Inventors: Edward Matthew Cooney, Jr., West Orange; Dennis Thomas Smialowicz, Waldwick, both of N.J.; James F. Tobey, Jr., 2155 Stonemill Dr., Salem, Va. 24153; Luiz Jiminez, Hackensack, N.J.

[73] Assignees: Reckitt & Colman Inc., Wayne, N.J.; James F. Tobey, Jr., Salem, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 08/694,188

[22] Filed: Aug. 8, 1996

Related U.S. Application Data

[63] Continuation of application No. 08/622,025, Mar. 26, 1996, abandoned.

[51] Int. Cl.$^6$ .............................. D06M 16/00; C12N 9/96; C12N 9/98; C02F 1/00
[52] U.S. Cl. .......................... 435/264; 435/187; 435/188; 210/601; 210/632
[58] Field of Search ..................................... 435/183, 187, 435/188, 195, 198, 201, 202, 219, 220, 221, 222, 223, 225, 264; 210/601, 632

[56] References Cited

U.S. PATENT DOCUMENTS

| | | | |
|---|---|---|---|
| 3,682,842 | 8/1972 | Innerfield | 510/530 |
| 3,720,606 | 3/1973 | Horney et al. | 424/76.8 |
| 3,915,853 | 10/1975 | Luck | 210/606 |
| 3,983,002 | 9/1976 | Ohya et al. | 435/209 |
| 4,305,837 | 12/1981 | Kaminsky et al. | 424/94.3 |
| 4,518,694 | 5/1985 | Shaer | 435/188 |
| 4,566,985 | 1/1986 | Bruno et al. | 134/42 |
| 4,610,800 | 9/1986 | Durham et al. | 435/264 |
| 5,449,619 | 9/1995 | Griffin et al. | 435/264 |
| 5,464,766 | 11/1995 | Bruno | 435/187 |
| 5,494,600 | 2/1996 | Surutzidis et al. | 435/187 |

OTHER PUBLICATIONS

George A. Jeffreys and Company, Inc., Tech Bulletin "Waste Bulletin 177–91–06", 1992, Salem, Virginia.

*Primary Examiner*—Leon B. Lankford, Jr.
*Assistant Examiner*—Christopher Tate
*Attorney, Agent, or Firm*—Fish & Richardson P.C.

[57] ABSTRACT

Aqueous septic tank maintenance compositions, process for their production, methods for their use as well as methods for the maintenance of sewage systems, particularly septic tanks and cesspools are provided. The aqueous septic tank maintenance compositions feature a high proportion of biologically active agents per unit volume or unit weight of the compositions, and reduced numbers of stabilizing compositions generally required to ensure storage and shelf stability of the biologically active agents contained therein. Processes for the production of these aqueous septic tank maintenance compositions, and methods for their use are also disclosed.

13 Claims, 1 Drawing Sheet

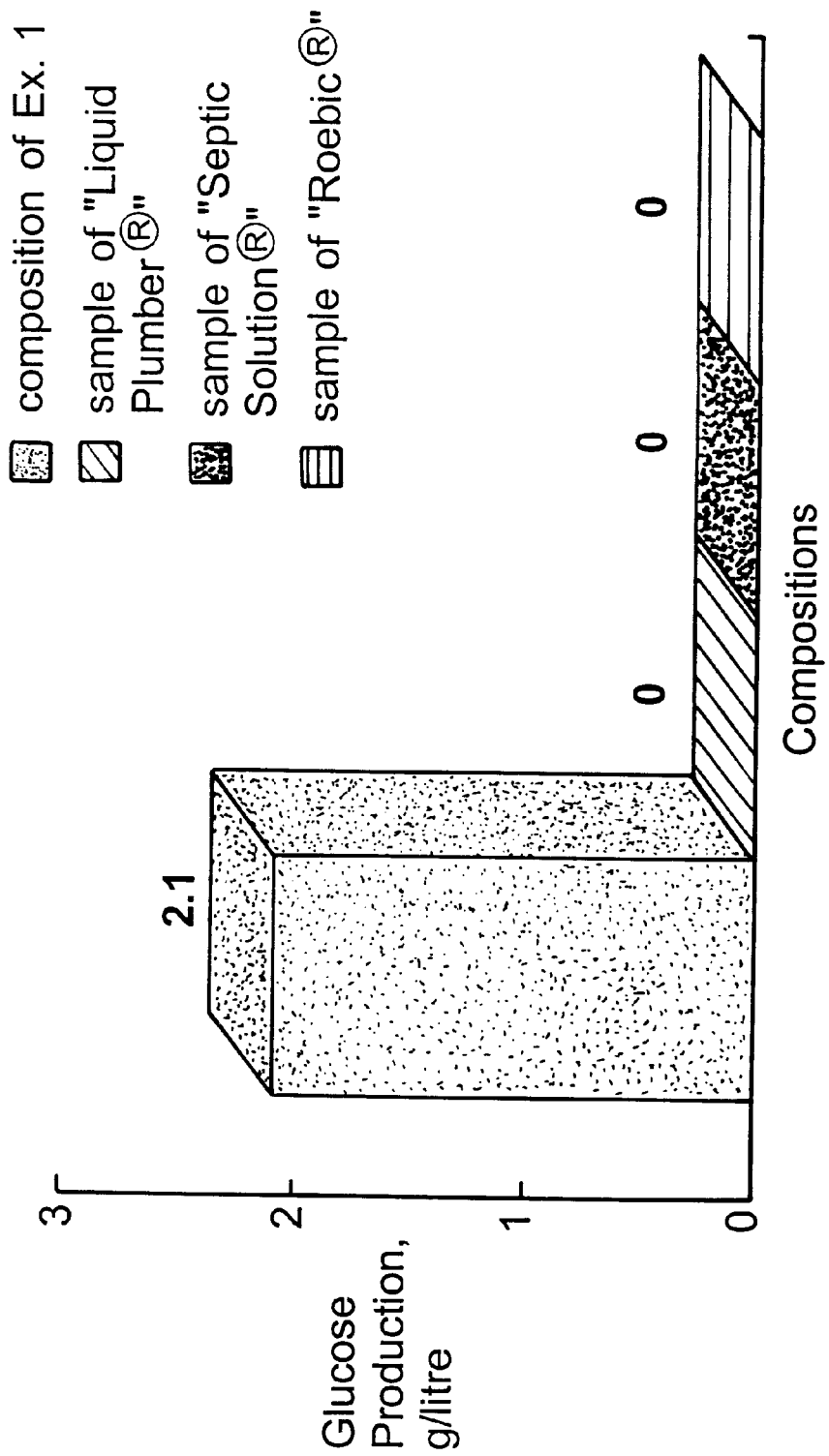

LIQUID SEPTIC TANK TREATMENT COMPOSITION

This is a continuation of application Ser. No. 08/622,025, filed Mar. 26, 1996, now abandoned.

The present invention relates to compositions useful for the treatment of sewage treatment systems, especially septic tanks and cesspools.

Treatment of sewage with microorganisms is known to the art. Many sewage treatment processes include a holding tank or vessel wherein the waste steam is acted upon by bacteria and other microorganisms, many of which may be naturally occurring, in order to at least partially break down or decompose the sewage. Examples of such holding tanks or vessels include septic tanks and cesspools wherein an entering waste stream is retained for a period of time, i.e., residence time, during which the present microorganisms act thereupon. Other holding tanks or vessels wherein such decomposition may take place include conventionally known sewage treatment plants which utilized anaerobic and/or aerobic or facultative holding pools, tanks or vessels for the treatment of sewage.

The waste streams associated with sewage may vary, and frequently may comprise various differing waste fractions, each of which present different specific requirements for their effective treatment. Typical waste stream fractions include "gray water" which are typically non-animal waste containing waters such water from washing and rinsing operations, and "black water". Such gray waters represent the fraction of the waste stream which is relatively easily disposed of, as they generally contain only a relatively small amount of organic compositions such as carbohydrates, fats and certain proteins found in detergent compositions and foods and may be suitable for direct reuse such as for irrigation purposes, or may be provided to a sewage treatment process. The further fraction, black water is the fraction which includes animal and human waste material containing waters which present a biohazard if not disposed of properly. Other fractions, such as improperly disposed of organic compositions such as paint compositions, oil compositions, as well as other solids such as fibrous materials such as paper, cotton and human hair may also be encountered in a waste stream and their disposal also needs to be properly addressed, and they normally comprise a considerable portion of the black water fraction. Typically, cellulose containing materials present in a waste stream include materials including toilet papers, sanitary napkins, tissues, and the like. These cellulose containing materials are present in significant amounts, and may comprise 15% and even more of the total solids content of a waste stream which may be gray and black water streams. This amount rises to an even more significant proportion when it is considered that the gray water fraction is separable from the black water fraction. Where gray water is at least partially removed, a corresponding concentration of such human, animal and other waste materials is produced, which can be considered to be a concentrated form of sewage. Further in view of the fact that there is a growing tendency to divide the waste stream into gray water and black water fractions, diverting the gray water and using it without any further treatment, and channeling the black water fraction to sewage treatment facilities as concentrated sewage, effective treatment of the concentrated sewage is necessitated. Especially in view of the biohazard potential that black water poses, it is thus increasingly important that the expedient breakdown and disposal of sewage occur, and that the continuing operation of sewage disposal facilities be assured.

As is also known to the art, various classes of microorganisms are effective in the treatment of waste streams, however very frequently these are effective in degrading only specific waste stream fractions, i.e., certain cellulase enzymes are known to be effective in the degradation of cellulose containing materials, such as paper. Certain proteolytic enzymes, particularly keratinases, are known to be somewhat effective in degrading hair. Similarly lipases known to be effective in the hydrolization of fats.

A technical problem of great concern is that in liquid formulations which comprise as one or more enzymes as active ingredients, there is also frequently required a large proportion of one or more stabilizing agents, and/or preservative agents which are directed to temporarily reducing the biological activity of a product formulation prior to its use. Such a requirement provides two constraints upon the types of formulations which may be produced. First, the necessity of substantial amounts of one or more stabilizing agents, and/or preservative agents limits the amount of enzymes which may be included in such a proposed formulation, particularly as it is generally conceded that with an increasing proportion of such enzymes in a formulation, a proportional increase in stabilizing agents, and/or preservative agents is also required. Second, as is known to the relevant art, it is not to be readily assumed that different classes of enzymes may be intermixed in a liquid formulation without the risk of destructive interaction between two or more enzymes. Accordingly, a substantial amount of one or more stabilizing agents, and/or preservative agents is usually dictated with the object of minimizing such possible interactions. In view of the above, the formulation of liquid compositions comprising a plurality of enzymes is clearly not a trivial task, particularly in view of the further fact that many chemical compositions and reagents are not biocompatible with one or more classes of enzymes, making successful formulations even more difficult. Notwithstanding these technical difficulties, various formulations and composition have been proposed in the art.

French Patent Application No. 80-10585 (Publication No. 2482130), published Nov. 13, 1981 to Societe Industrielle Des. Produties Chimiques Lumer describes a process for the preparation of inoculum for maintenance of septic tanks and the like comprising dehydrated microorganisms and enzymes, as well as inocula prepared by the described process. Taught therein are certain dry powdery preparations which comprise a dehydrated microorganism prepared from the culture strain of species normally present in septic tanks and/or digesters which are prepared for the use of a zeolite to which is further added a powdered nonionic dispersant. The powdered preparation is usefull in the reseeding of septic tanks, cesspools, and other like vessels wherein the digestion of organic materials such as waste, sewage sludges, and the like are digested and/or partially broken down by the action of certain species of enzymes.

U.S. Pat. No. 3,720,606 provides a formulation for the treatment of sewage and other odor causing matter which includes the use of a aerobic, mesophilic, spore forming bacteria.

Currently, co-pending U.S. patent application Ser. No. 08/164,609 which is commonly assigned, teaches a sewage treatment composition which comprises Bacillus species cultures in combination with a fungal cellulase which are cited as providing a synergistic degradation of cellulose such as may be found in sewage treatment vessels such as septic tanks and/or cesspools.

Thus, while the foregoing provide a variety of compositions and processes for sewage decomposition and particularly septic system maintenance, these formulations are not without attendant shortcomings. For example, certain of these compositions are available only in a powdered form. While such a powdered form generally requires a reduced amount of preservative and/or stabilizing effective constituents in their formulations, there is also a known prejudice of consumers, especially domestic and household consumers against non-liquid formulations. Such non-liquid formulations are not necessarily easy to measure out or use, and more significantly, there is frequently a hesitancy by such consumers to introduce a dry material composition into a drain or toilet for the fear that such may cause a blockage or clog.

A further shortcoming of certain prior art compositions is that they frequently require multiple dosings, particularly multiple dosings at particularly high enzymatic concentration levels such that an effective amount of the active enzyme constituent(s) is properly delivered into the sewage treatment system, especially to the interior volume of the septic tank or cesspool. Further, many of the enzymatic compositions are of only limited spectrum use, i.e., in that they comprise one or two enzymes which are known to attack certain target types of deposits, i.e., proteases which are effective at reducing deposited proteins. However, many such enzymatic compositions are limited in that it is also known to the art that compositions comprising a plurality of enzymes are not necessarily easy to produce in a liquid form, as it is likely that one or more of the enzymes may attack another enzyme or other constituent of the liquid composition wherein the attacked enzyme or liquid constituent is a good substrate for the attacking enzyme. Further, as had been previously noted, the biocompatibility of plural compositions of enzyme mixtures is difficult to produce and even more difficult to maintain over a period of time. Thus, many known compositions comprise a significant proportion, even relatively higher proportions, of one or more preservative agents which act to reduce or minimize the enzymatic activity of one or more of the biological components of such mixtures. While these may be effective, they also pose the risk of being a useful substrate, viz., a food source for one of the bacteria and/or one of the enzymes for which they are intended to be a preservative, a further problem attendant upon such mixtures is that with increasing amounts and/or with differing amounts of enzymes which are intended to be included with the composition, very frequently one or more dissimilar types of preserving agents must be provided in an ever increasing amount so to offset the tendency of the enzymes to feed and breakdown one or more of their co-components in such a mixture. This necessarily leads to diminished amount of the effective or "active" biological constituents in such a composition due to the increased proportion of the necessary preserving agents. From the foregoing then, it will be apparent that there is a real and continuing need in the art of drain maintenance products to address one or more of the technical shortcomings noted above. The present invention addresses one or more of the shortcomings and successfully overcomes them in preferred embodiments which overcome all of these shortcomings recited above.

It is an object of the invention to provide improved formulations of enzyme containing septic tank maintenance compositions, particularly in liquid form, which are particularly effective in accelerating the decomposition of solid waste materials in a sewage treatment system.

It is a further object of the invention to provide an aqueous septic tank maintenance composition which uses enzymes as active constituents and which is particularly effective in accelerating the decomposition of solid waste materials in a sewage treatment system.

It is a still further object of the invention to provide a process for sewage treatment systems, including septic tanks and cesspools having a tendency to accumulate undesired deposits, such process comprising the step of adding a septic tank maintenance composition as taught herein in effective amounts and reducing such deposits. Such application may be a one-time application, or may include periodic applications of the septic tank maintenance compositions.

It is a yet further object of the invention to provide improved septic tank maintenance compositions based on biologically active agents in which said biologically active agents are present in increased proportions.

A further object of the invention is to provide new and improved septic tank maintenance compositions, particularly liquid forms thereof, which have reduced numbers of non-active constituents.

It is a still further object of the invention to provide an improved process for the formulations of enzyme containing septic tank maintenance compositions, particularly in liquid form, which septic tank maintenance compositions are particularly effective in accelerating the decomposition of solid waste materials in a sewage treatment system.

These and other objects of the invention will become more apparent from the reading of the specification herein.

The compositions of the present invention are aqueous compositions effective as septic tank or cesspool treatment compositions which include the following constituents:

A) a bacteria/enzyme complex;
B) an organic solvent;
C) water

The aqueous compositions according to the invention may include one or more further optional constituents D) including many which are known to the art such as rheology modifying agents including thickeners, coloring agents pigments, dyes), opacifiers, fragrances whether naturally occurring or synthetically produced, fillers, pH adjusting agents, buffers, as well as other conventionally known additives which however desirably are not a food source for the bacteria. As a further optional constituent amounts of micronutrients for the bacteria may also be present in the inventive compositions.

FIG. 1 illustrates a comparative evaluation of cellulose degradation characteristics of compositions according to the instant invention as compared to several commercially available septic tank treatment preparations.

Recited as Constituent A, the bacteria/enzyme complex according to the invention includes at least one enzyme and at least one microorganism which is capable of producing a hydrolytic enzyme. Exemplary enzymes include cellulases, amylases, proteases and lipases, among which cellulases and lipases are preferred. These enzymes, as well as commercially available enzymatic preparations comprising the same are known to the art and are available from a variety of commercial suppliers. Alternatively, enzymatic preparations comprising these proteases may be produced by conventional methods, i.e., by extraction from a microorganism which is known to produce the desired enzyme under controlled laboratory conditions or in the alternative, in a bioreactor.

Cellulase is a term generally used to described the group of enzymes which hydrolyze cellulose. As is known, cellulose is a major constituent of paper products, and the use of cellulose is also becoming increasingly known to be an additive to certain foodstuffs. Thus, they are expected to constitute an appreciable portion of a waste stream.

Cellulases include one or more subcategories of enzymes which hydrolyze cellulose which subcategories include endocellulases, exocellulases, beta-1,3-glucanases and beta-glucosidases. In the compositions and processes according to the present invention, any of these cellulases may be used alone or in combination but are used preferably in combination. Preferred cellulases for use include those which are derived from microorganisms of the genus Trichoderama, Chrysosporium, Aspergillus, Penicillium, Fusarium, Thielavia, Sporotrichium, Celluominas, Ruminococcus, and Clostridium. Cellulases are also known to be produced by genetically engineered microorganisms of the genus Bacillus. Particularly preferred microorganisms useful as a source of the cellulase constituent include *Aspergillus niger, Aspergillus aculeatus, Bacillus subtilis, Trichoderma longibrachiatum*, and *Bacillus lentus*. Commercial sources for these cellulases are well known. Examples include those marketed under the tradenames MAXICEL available from the Geo. A. Jeffreys Co., Inc. (Salem Va.) as well as CELLUCLAST 250 1 and CELLUCLAST 100 1 available from Novo Nordisk, Inc., (New York, N.Y.).

The activity of the cellulase enzymes may be expressed in units of cellulase units per gram; desirably the cellulase constituent exhibits an activity of at least about 100,000 CU units/gram, and still more desirably the constituent exhibits an activity of at least 200,000 CU units/gram, at a pH of 7.0. These CU units/gram may also be interchangeably expressed as CMC units determined by known viscosity measurement techniques, which techniques are known and recognized in the art. The cellulase enzyme further desirably exhibits activity in the pH range of about 4.0 to about 9.5, but preferably exhibits activity at a pH in the range of about 5.5 to about 7.5.

Cellulases may also be prepared from certain fungi, which are known to produce cellulase, and such cellulases harvested from fungi may also be used in the compositions of the invention.

Lipases which find use in the compositions of the invention are any which are found effective in the reduction of fats and oils. Fats which are particularly susceptible to decomposition by lipases find their origin in animal or plants. Such fats are generally deposited as food residues which are introduced into a drain and drain conduit as they are expected to constitute an appreciable portion of a waste stream. Fats and oils, particularly those which are solidified in a non-fluid form are also known to be an extremely difficult deposit to remove due to the hydrophilic nature of fats which resist dissolution in water.

In the compositions according to the invention, any lipase which is effective in the degradation of fats or oils which find their origin in animals or plants may be used. Useful lipases may be derived from a variety of sources including microorganisms of the genus Aspergillus, Rhizomucor and Candida. Particularly preferred microorganisms include those which include *Aspergillus niger, Aspergillus oryzae, Rhizomucor miehei, Candida rugosa*. Lipases which also may be used include those which may be derived from animal sources such as from animal pancreatic tissues as from forestomachs of certain livestock including calves, kids and lambs.

The activity of the lipases may be expressed in various units, including the units of fatty acid (butyric acid) liberated from tributyrin, at pH 7.0 and 30° C. Such units are also interchangeably referred to as lipase units or "LU". Desirably, the lipases exhibit at least about 1,000 units butyric acid units liberated from tributyrin at pH 7.0 and 30° C. per gram, more desirably at least about 5,000 units/gram, and most desirably at least about 10,000 units/gram under these temperature and pH conditions.

The pH ranges wherein the lipases exhibit useful activity is between about 5.0–about 13.5, but more desirably is between about 7.0–12.0.

Various commercially available lipase containing preparations are available, such as LIPIDASE from available from the Geo. A. Jeffreys Co., Inc. (Salem Va.) and which is described to be a lipase from a fungal origin, which exhibits an enzyme activity level of at least about 10,000 butyric acid units liberated from tributyrin at pH 7.0 and 30° C. per gram, and which is useful in the pH range of 5.0–13.5.

Lipases may also be prepared from certain fungi, which are known to produce lipases, and such lipases harvested from fungi may also be used in the compositions of the invention.

Proteases form a part of Constituent A according to the invention. Any proteases which are effective in breaking down proteins, particularly animal proteins may be used in the compositions according to the invention. Useful proteases may be derived from a variety of sources, including microorganisms such as those of genus Aspergillus, and Bacillus. Particularly, proteases derived from microorganisms *Aspergillus niger, Aspergillus oryzae, Bacillus licheniformis*, and *Bacillus subtilis* are advantageously used.

The activity of proteases may be described as protease units/gram which is established by known methods. Desirably the protease constituent exhibits an activity of at least about 100,000 protease units/gram, and still more desirably constituent exhibits an activity of at least 250,000 protease units/gram, but most desirably constituent exhibits an activity of at least 400,000 protease units/gram. These protease units/gram are interchangeably referred to as "CDU units/gram", or casein digestion units/gram which are known to the art and are determinable by well known techniques. The proteases further desirably exhibit activity in the pH range of about 3.5 to about 13.0, but preferably exhibit activity at a pH in the range of about 7.0 to about 10.5.

Various commercially available lipase containing preparations are available, such as ALKAPRO from available from the Geo. A. Jeffreys Co., Inc. (Salem Va.) and which is described to be an alkaline serine type protease from a bacterial origin, which exhibits an enzyme activity level of at least about 400,000 protease units/gram and which is useful in the pH range of 3.5 to about 13.0, and which exhibits optimal activity at a pH in the range of about 7.0 to about 10.5.

Proteases which may be derived from other sources other than those elucidated above may also be used.

Amylases which find use in Constituent A include those which are effective in the breakdown of starches into sugars. Such useful amylases include those which are referred to as alpha-amylases, beta-amylases, iso-amylases, pullulanases, maltogentic amylases, amyloglucosidases, and glucoamylases as well as other amylase enzymes not particularly elucidated here. These include endo-active, and exo-active amylases. Useful amylases may be obtained from a wide variety of sources, including microorganisms of the genus: Aspergillus, Rhizopus, and Bacillus. By way of non-limiting example, specific microorganisms include: *Aspergillus niger, Aspergillus oryzae, Rhizopus oryzae, Rhizopus niveus, Bacillus subtilis, Bacillus amyloliquefaciens, Bacillus stearothermophilus, Bacillus licheniformis* especially containing a *Bacillus stearothermophilus* gene for alpha-Amylase, *Bacillus subtilis* containing a *Bacillus megaterium* gene for alpha-Amylase, as well as *Bacillus acidopullulyticus*. Other sources include for example, barley malt, certain animal pancreatic tissue as well as others not elucidated here but which are nonetheless known to the art.

The activity of amylases may be described in units of bacterial amylase units per gram according to known methods such as those disclosed in the Food Chemicals Codex. Useful amylase containing preparations contain at least about 10,000 bacterial amylase units per gram (BAU/g), more desirably at least about 18,000 BAU/g, and most desirably at least about 22,000 BAU/g. Such BAU units may be determined by known techniques.

Useful amylase containing preparations are available from a variety of commercial sources including for example, a product marketed as IC 24,000 by the Geo. A. Jeffireys & Co., Inc. (Salem Va.) and which is described to be an amylase/carbohydrase preparation from a bacterial origin, which exhibits an enzyme activity level of at least about 24,000 bacterial amylase units per gram.

Optionally but desirably Constituent A may further comprise amounts of further secondary enzymes including but not limited to: pectinase, carbohydrase, beta-glucanase, hemicellulase and xylanase. The addition of such further secondary enzymes such as pectinase aids in the decomposition of fruit containing wastes, carbohydrases effective in breaking down non-starch polysaccharides, beta-glucanase aids in the breakdown of vegetable gums, and xylanase assists in the decomposition of various types of polymeric gums and natural polymers.

In addition to the enzymes described above, Constituent A desirably further includes one or more microorganisms or other source for the enzymes described as present in Constituent A. Most desirably, Constituent A includes an amount of at least one microorganism which is suited for the generation of at least one enzyme selected from: amylases, proteases, lipases or cellulases. More desirably Constituent A includes amounts of at least one or more microorganisms suited for the generation of two or more enzymes selected from: amylases, proteases, lipases or cellulases, but most desirably Constituent A includes amounts of at least one or more microorganisms suited for the generation of each enzyme of the group: amylases, proteases, lipases and cellulases. Various sources for such enzymes, particularly those described above in conjunction with the description of the respective enzymes may be utilized. As enzyme producing microorganisms, fungi and bacteria are especially preferred for use as the source of enzymes.

Methods for the production of preparations such as those described above are known, and include for example the processes as described in U.S. Pat. No. 2,505,360 the contents of which are herein incorporated by reference.

Recited as Constituent B in the present inventive liquid compositions is an organic solvent which is soluble or at least partially miscible in water, and which is further effective as an enzymatic stabilizer constituent which acts to effectively reduce the biological activity of the enzyme, a bacterial culture complex and, and/or the enzyme complex, most particularly the cellulase enzymes. As is recognized amongst skilled practitioners, enzymes particularly cellulase enzymes, are generally considered to be unstable in aqueous formulations especially over extended periods of time. To overcome this technical shortcoming, the prior art provides teachings of various stabilizers systems generally including a number of various stabilizer constituents which are directed to enhancing the stability of enzymatic constituents in liquid compositions particularly for extended periods of time which enhances the shelf life and/or storage life of a formulation.

In accordance with the present invention, the inventors have surprisingly found that a reduction in the number of stabilizer constituents as compared to prior art multiple enzyme comprising liquid compositions, particularly cellulase enzyme comprising liquid compositions may be achieved by the judicious selection of the types and amounts of organic solvents as well as the amount of any water which is formed into such liquid compositions. The inventors have found that the use of two or fewer, and most preferably a single organic solvent constituent effectively and simultaneously provides an effective stabilizing effect for multiple enzyme comprising liquid compositions, particularly cellulase enzyme comprising liquid compositions, as well as acting as a liquid carrier medium for such multiple enzyme comprising liquid compositions. Still further the use of such reduced numbers of stabilizer components, most especially the use of only a single organic solvent has been observed to generally dispense with the need for any surfactant compositions which are known to the art and in general usage in such multiple enzyme comprising liquid compositions, particularly cellulase enzyme comprising liquid compositions.

In accordance with the present inventive teaching, particularly useful organic solvents providing this effect include $C_{1-5}$ alcohols, $C_{1-5}$ polyols and glycols, polyethylene glycol, polypropylene glycol, any of which may be interrupted by an oxygen so to form the corresponding ether, as well as sorbitol. These organic solvents may be used individually or in mixtures of two or more, but are desirably used individually, and generally may comprise up to about 60% by weight of the liquid compositions according to the invention. Such organic solvents are liquids at room temperature (approximately 68° F., 20° C.), feature good aqueous solubility, and importantly, have been found to be effective in stabilizing the biologically active constituents of the liquid compositions. Preferred amongst these organic solvents are propylene glycol and glycerol, both of which have been found by the inventors to provide the beneficial effects noted above, and which are inexpensive and readily available. Desirably, propylene glycol is used in amounts of up to about 33% by weight of the liquid compositions, and more desirably is present in amounts of from 7.5%–33% by weight of the liquid compositions. Desirably, glycerol is is used in amounts of up to about 55% by weight of the liquid compositions, and more desirably is present in amounts of from 40%–55% by weight of the liquid compositions When present, the organic solvent is desirably present in a stabilizing effective amount, that is to say in an amount which is found effective in reducing the biological activity of the biologically active constituents in the inventive liquid compositions. As it is known to the art, water is a medium effective as a carrier for enzymes, but one in which the enzymes are active, a technical result which is not always desired in a commercial product which is to have an appreciable shelf life, i.e., in excess of several weeks and particularly in excess of two or more months. Thus, the art has in the past turned to dehydrated formulations as it is known that certain enzymes may be immobilized by dehydration or lyophilization and thus preserve the enzymes from denaturation. In the alternative, the prior art has also provided formulations which included a large proportion of stabilizing agents generally, one or more stabilizing agents. Further, these stabilizing agents were generally utilized in conjunction with one or more preservatives such as for example, alkali metal salts such as NaCl, $NaSO_4$, $Na_2SO_4$, as well as various calcium salts such as $CaCl_2$ and $CaCO_3$, and mixtures thereof. The use of such alkali metal salts has also been known to be useful in large amounts such as fillers.

The present inventors' discovery is that through the judicious selection of the organic solvent constituent as well as its inclusion in appropriate amounts, it is possible to provide excellent liquid septic tank maintenance compositions which exhibit good shelf storage stability, good activity in their intended application, and which are formed with a substantially reduced number of constituents over prior art liquid compositions intended for the same application. The technical significance and benefits of such formulations include, but are not limited to: production of formulations comprising a higher content of biologically active agents per unit volume of the formulation; reduced number of separate constituents providing ease of formulation and more importantly reduced risks in the likelihood of incompatibility between a biologically active constituent and a nonbiologically active constituent; favorable long term efficacy of formulations and commercially prepared products based on such formulations; and, ease of handling and of use when compared to non-liquid formulations directed to septic tank maintenance applications. It is not believed by the inventors that such a liquid formulation providing such technical benefits has hithero been available to the art. The inventors further believe that such compositions may be achieved is surprising as from the prior art was known that where a higher biological activity was provided on a unit volume or unit weight basis of such a formulation, a significant proportion of each such unit volume or weight was comprised of stabilizer and/or preservative constituents directed to limiting the biological activity of such liquid compositions, particularly enzymes. Concomitantly, any desired increase in biological activity of such a formulation per unit volume or unit weight basis was believed to require a proportional increase in the proportion of stabilizer and/or preservative constituents.

Recited as Constituent C, water, is also included in the liquid compositions according to the invention. Water is added to the other recited constituents in order to provide 100% by weight of a liquid composition in accordance with the present inventive teaching. The water may be tap water, but is preferably distilled and/or deionized water. If the water is tap water, it is preferably appropriately filtered in order to remove any undesirable impurities such as organics or inorganics, especially minerals salts which are present in hard water which may thus interfere with the operation and/or stability of the compositions, particularly the biologically active constituents.

While not essential to the successful operation of the liquid compositions taught herein, nor to be considered amongst the essential constituents of the present inventive liquid compositions, the compositions of the invention can also include further optional constituents which may be present in any amount which is not found to substantially deactivate the biologically active constituents, or to otherwise act as a food source for the bacteria which is present in the liquid compositions. The inclusion of one or more such further optional constituents may indeed enhance or improve the compositions, particularly from a cosmetic or consumer standpoint. Exemplary optional constituents include rheology modifying agents including thickeners, coloring agents such pigments and dyes, opacifiers, fragrances whether naturally occurring or synthetically produced, fillers, pH adjusting agents, buffers, surfactants for the solubilization of fats and oils, as well as other conventionally known additives.

Further optional constituents which may be included in the liquid compositions but which might be considered a food source for the bacteria are micronutrients. Such are known to the art as being useful for maintaining the viability of the bacteria in compositions for extended periods of time, i.e., several months. Such micronutrients are known to the art, and include preparations which include calcium salts, magnesium salts and other salts as well.

These further optional constituents, in total, generally comprise no more than 5 parts by weight of the liquid compositions of the invention, based on the total weight of such a composition.

In the liquid compositions according to the invention it may be desirable to include an effective amount of a buffering agent which will tend to retain the pH of the liquid compositions within acceptable limits, i.e., within limits which will not adversely affect the activity of the biologically active constituents in the liquid preparations taught herein. Examples of buffers include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use buffers such materials as borates, aluminates and certain organic materials such as gluconates, succinates, maleates, and their alkali metal salts. These buffers are generally necessary in only minor amounts, generally in amounts of no more than 5 parts by weight based on the total weight of a liquid composition, but desirably are present in substantially lesser amounts, such as in amounts of no more than 1 part by weight based on the total weight of a liquid composition. Desirably, the selected buffer will maintain the pH of the liquid compositions of the invention within the active range for the selected enzymes and microorganisms present, but it is not to be confused with other stabilizer constituents which are directed to reducing or minimizing the denaturation and activity of the biologically active constituents of the invention.

Particularly useful pH ranges for the liquid composition are from about 4.5 to about 9.5, but more desirably are in the range of from 6.0 to 8.0.

As will be appreciated by skilled practitioners in the art, the dosage, frequency of use, as well as the concentration of the active ingredients in the compositions of the invention are interdependent variables which are further influenced by the environment within which the compositions are to be used, as well as the operating parameters of the sewage treatment vessel (size, configuration, average residence time of sewage, activity of microorganisms already present in the sewage treatment vessel, etc.) being treated. Determination of these variables may be accomplished by routine methods, in manners known to the skilled practitioner, and the dosage and concentration of the active ingredients in the compositions may be accordingly established. By way of example, where the compositions are used as a septic tank additive for a conventional septic tank having an operating capacity of about 1000 gallons, an effective dosage amount of the liquid compositions of the invention is about 1 to 10 fluid ounces, and more preferably about 7 to about 9 fluid ounces. Of course it is to be understood that these dosage amounts are based upon a septic tanks having an operating capacity of 1000 gallons, and that the effective dosage may be proportionally adjusted for septic tanks having higher or loser operating capacities. Further, it is to be understood that wide variations in the dosage amounts and dosing frequency are possible, in which case more frequent and/or multiple dosages would be preferred.

As used throughout this specification and in the accompanying examples below, the terms "parts by weight" or "percentage weight" are used interchangeably in the specification and in the following examples wherein the weight percentages of each of the individual constituents are indicated in weight percent based on the total weight of the particular composition of which it forms a part, unless indicated otherwise.

As can be seen from the above, the present inventors have provided new and useful treatment compositions which are particularly effective, and which contain a high ratio of active agents per unit volume or unit weight of the compositions. The compositions are also particularly shelf stable, thus permitting their extended storage and enhancing the useful life of the commercially prepared product form. Exemplary embodiments of compositions within the scope of the invention are illustrated in the Examples below. While described in terms of one or more presently preferred embodiments, it is to be understood that the present disclosure is to be interpreted as by way of illustration, and not by way of limitation, and that various modifications and alterations apparent to one skilled in the art may be made without departing from the scope and spirit of the present invention.

EXAMPLES—FORMULATIONS

Several exemplary and preferred formulations of liquid compositions according to the invention, each of which was formed by simple mixing of the noted constituents in measured amount to the volume of water using manual or mechanical stirring are described below. All of the proportions are listed in parts by weight based on the total overall weight of the particular formulation.

Example 1

A 1 liter amount of a liquid composition according to the invention was produced which included the following constituents which are indicated in units of activity, or in weight percent (% wt.) based on the total weight of the composition. It is to be noted that the aqueous bacteria complex and enzymes were provided in aqueous compositions which aqueous portions provided the aqueous content of the liquid compositions, as well as any further added water.

EXAMPLE 1 formulation

| Constituent: | quantity: |
|---|---|
| aqueous bacteria complex | 2.1 × 10⁸/ml |
| protease enzyme | 2,700 CDU/ml |
| amylase enzyme | 18,000 BAU/ml |
| lipase enzyme | 14 LU/ml |
| cellulase enzyme | 1,400 CU/ml |
| propylene glycol | 20% wt. |
| glycerol | — |
| dye | 0.0005% wt. |
| perfume | — |
| water | to 100% wt. |

The amounts of the aqueous bacteria complex are indicated in colony forming units per milliliter. Where present, the dye and perfume were inert relative to the bacteria and were not a food source, thus their presence posed no detrimental effect to the activity of either the enzymes or the bacteria in the liquid compositions.

Example 2

A 1 liter amount of a further liquid composition according to the invention was produced which included the following constituents which are indicated in units of activity, or in weight percent (% wt.) based on the total weight of the composition. The individual constituents used are the same as described in Example 1.

EXAMPLE 2 formulation

| Constituent: | quantity: |
|---|---|
| aqueous bacteria complex | 1.0 × 10⁶/ml |
| protease enzyme | 1,200 CDU/ml |
| amylase enzyme | 8,000 BAU/ml |
| lipase enzyme | 8 LU/ml |
| cellulase enzyme | 640 CU/ml |
| propylene glycol | 20% wt. |
| glycerol | — |
| dye | — |
| perfume | — |
| water | to 100% wt. |

The amounts of the aqueous bacteria complex are indicated in colony forming units per milliliter.

Example 3

A 1 liter amount of a further liquid composition according to the invention was produced which included the following constituents which are indicated in units of activity, or in weight percent (% wt.) based on the total weight of the composition. The individual constituents used are the same as described in Example 1.

EXAMPLE 3 formulation

| Constituent: | quantity: |
|---|---|
| aqueous bacteria complex | 2.1 × 10⁸/ml |
| protease enzyme | 1,200 CDU/ml |
| amylase enzyme | 8,00 BAU/ml |
| lipase enzyme | 8 LU/ml |
| cellulase enzyme | 640 CU/ml |
| propylene glycol | — |
| glycerol | 50% wt. |
| dye | — |
| perfume | — |
| water | to 100% wt. |

The amounts of the aqueous bacteria complex are indicated in colony forming units per milliliter.

Example 4

A 1 liter amount of a further liquid composition according to the invention is produced which includes the following constituents which are indicated in units of activity, or in weight percent (% wt.) based on the total weight of the composition. The individual constituents used are the same as described in Example 1.

EXAMPLE 4 formulation

| Constituent: | quantity: |
|---|---|
| aqueous bacteria complex | 1.0 × 10⁸/ml |
| protease enzyme | 1,200 CDU/ml |
| amylase enzyme | 8,000 BAU/ml |
| lipase enzyme | 150 LU/ml |
| cellulase enzyme | 640 CU/ml |
| propylene glycol | 20% wt. |
| glycerol | — |

EXAMPLE 4-continued

| formulation | |
|---|---|
| Constituent: | quantity: |
| dye | 0.0005% wt. |
| perfume | — |
| water | to 100% wt. |

The amounts of the aqueous bacteria complex are indicated in colony forming units per milliliter.

Example 5

A 1 liter amount of a further liquid composition according to the invention is produced which includes the following constituents which are indicated in units of activity, or in weight percent (% wt.) based on the total weight of the composition. The individual constituents used are the same as described in Example 1.

EXAMPLE 5

| formulation | |
|---|---|
| Constituent: | quantity: |
| aqueous bacteria complex | $1.0 \times 10^8$/ml |
| protease enzyme | 1,200 CDU/ml |
| amylase enzyme | 8,000 BAU/ml |
| lipase enzyme | 8 LU/ml |
| cellulase enzyme | 10,000 CU/ml |
| propylene glycol | — |
| glycerol | 50% wt. |
| dye | — |
| perfume | 0.3% |
| water | to 100% wt. |

The amounts of the aqueous bacteria complex are indicated in colony forming units per milliliter.

EXAMPLES—EFFICACY

The efficacy of certain of the example formulations in the degradation of cellulose to glucose was evaluated in accordance with the general test protocol, following.

Sample preparations based on commercially available septic tank preparations were prepared by providing a measured amount of such a septic tank treatment preparation (described below) to a measured quantity of water in order to prepare an aqueous dilution. These dilutions corresponded to the proper septic tank dosage and resulting dilutions as per label directions provided with such a product.

Sample preparations in accordance to the invention were supplied at the preferred dilution of 7–9 fluid ounces per 1000 gallons of water. To each sample was provided a standard sample amount of toilet paper, and each of the sample preparations were permitted to incubate at approx. 25° C. for 3 days. Afterwards, 2 ml aliquots of the sample preparations were added to test tubes, which were optionally filtered, to which was subsequently added 2 ml of a reagent composition of a 1% solution of 3,5-dinitro-salicylic acid in a alkaline sodium hydroxide solution which further included an appreciable concentration of sodium potassium tartrate. Such a reagent is known to the art, and it is further known to react with reducing groups of free sugar molecules in a color producing reaction, such free sugars resulting from the hydrolysis of cellulose catalyzed by cellulase. The test tubes were then boiled, then quenched in an ice bath to cool their contents to room temperature (approx. 20° C.). Afterwards, 20 ml of water was added to the contents of each test tube, and the results were well mixed. The absorbance at a wavelength of 540 nanometers of each sample was determined to determine the amount of sugar present in the respective test tube. These amounts were compared against the absorbency of standardized samples having known amounts of sugar present.

As comparative examples, samples of certain commercially available preparations directed to septic tank maintenance compositions were produced by following the instructions of the label on the respective package. These comparative samples were evaluated against liquid compositions noted on Table 1, the results of which are noted on Table 2, below, as well as on FIG. 1.

TABLE 2

| CELLULOSE DEGRADATION | |
|---|---|
| Sample: | production of glucose, g/liter: |
| composition of Ex. 1 | 2.10 |
| sample of "Liquid Plumber ®" | 0.00 |
| sample of "Septic Solution ®" | 0.00 |
| sample of "Roebic ®" | 0.00 |

The commercial product, "Liquid Plumber®" is a septic tank treatment composition in liquid form which is commercially marketed by the Clorox Corporation. The commercial product, "Septic Solution®" is a septic tank treatment composition in liquid form which is commercially marketed by the Earthcare Products Division of US Biotech Inc. The commercial product "Roebic®" is is a septic tank treatment composition in liquid form which is commercially marketed by Roebic Labs Inc.

As can be seen from the foregoing table as well as from FIG. 1, the biodegradative ability of known art septic tank maintenance compositions to reduce cellulose, a major component of paper products including toilet paper, sanitary napkins, paper towels, tissues and other paper products which are expected to be found in sewage treatment systems, particularly septic tanks and cesspools as noted, supra. As can be observed by the results above, the efficacy of the commercially available preparation in their ability to break down cellulose was substantially less than the present inventive compositions.

We claim:

1. An aqueous septic tank and cesspool treatment composition comprising:
    a bacterial/enzyme complex which includes:
        at least one type of bacteria present in an amount of at least about $1.0 \times 10^6$ colony forming units/mL;
        cellulase enzymes exhibiting an activity of at least about 640 CU/mL;
        lipase enzymes exhibiting an activity of at least about 8 LU/mL;
        protease enzymes exhibiting an activity of at least about 1,200 CDU/mL; and
        amylase enzymes exhibiting an activity of at least about 8,000 BAU/ml;
    a stabilizing effective amount of a single organic solvent selected from $C_{1-5}$ alcohols, $C_{1-5}$ polyols, glycols, and sorbitol; and, water.

2. The aqueous composition according to claim 1 which includes cellulase enzymes exhibiting a combined activity of at least 200,000 CU units/gram at a pH of 7.0.

3. The aqueous composition according to claim 1 which includes lipase enzymes exhibiting a combined activity of at least 10,000 LU units/gram at a pH of 7.0.

4. The aqueous composition according to claim 1 which includes protease enzymes exhibiting a combined activity of at least 400,000 protease units/gram at a pH of 3.5–13.0.

5. The aqueous composition according to claim 1 which includes amylase enzymes exhibiting a combined activity of at least about 18,000 BAU/g.

6. The aqueous composition according to claim 1 which further comprises one or more secondary enzymes selected from pectinase, carbohydrase, beta-glucanase, hemicellulase and xylanase.

7. The aqueous composition according to claim 1 which further comprises a micronutrient.

8. The aqueous composition according to claim 1 which further comprises a surfactant.

9. The aqueous composition according to claim 1 which further comprises a coloring agent.

10. The aqueous composition according to claim 1 which further comprises a fragrance.

11. An aqueous septic tank and cesspool treatment composition comprising:
a bacterial/enzyme complex which includes:
at least one type of bacteria present in an amount of at least about $1.0 \times 10^6$ colony forming units/mL;
cellulase enzymes exhibiting an activity of at least about 640 CU/mL;
lipase enzymes exhibiting an activity of at least about 8 LU/mL;
protease enzymes exhibiting an activity of at least about 1,200 CDU/mL; and
amylase enzymes exhibiting an activity of at least about 8,000 BAU/mL;
propylene glycol present at about 20% by weight; and, water.

12. An aqueous septic tank and cesspool treatment composition comprising:
a bacterial/enzyme complex which includes:
at least one type of bacteria present in an amount of at least about $1.0 \times 10^6$ colony forming units/mL;
cellulose enzymes exhibiting an activity of at least about 640 CU/mL;
lipase enzymes exhibiting an activity of at least about 8 LU/mL;
protease enzymes exhibiting an activity of at least about 1,200 BAU/mL;
amylase enzymes exhibiting an activity of at least about 8,000 BAU/mL
glycerol present from about 40% to about 55% by weight; and, water.

13. A method of treating a septic tank or cesspool with an aqueous composition, said method comprising providing from 1 to 10 fluid ounces of an aqueous composition per 1000 gallons of septic tank or cesspool volume into a septic tank or cesspool, said aqueous composition comprising:
(a) a bacterial/enzyme complex which includes:
at least one type of bacteria present in an amount of at least about $1.0 \times 10^6$ colony forming units/Ml;
cellulase enzymes exhibiting an activity of at least about 640 CU/Ml;
lipase enzymes exhibiting an activity of at least about 8 LU/Ml;
protease enzymes exhibiting an activity of at least about 1,200 CDU/Ml; and
amylase enzymes exhibiting an activity of at least about 8,000 BAU/ml;
(b) a stabilizing effective amount of an organic solvent selected from $C_{1-5}$ alcohols, $C_{1-5}$ polyols, glycols, and sorbitol; and,
(c) water.

* * * * *

UNITED STATES PATENT AND TRADEMARK OFFICE
CERTIFICATE OF CORRECTION

PATENT NO. : 5,905,037
DATED : 18 May 1999
INVENTOR(S) : Edward Matthew COONEY, Jr.; Dennis Thomas SMIALOWICZ; James F. TOBEY, Jr. and Luiz JIMINEZ It is certified that error appears in the above-identified patent and that said Letters Patent is hereby corrected as shown below:

At column 16, line 6, change "cellulose" to --cellulase--.
At column 16, line 22, change "Ml" to --mL--.
At column 16, line 24, change "Ml" to --mL--.
At column 16, line 26, change "Ml" to --mL--.
At column 16, line 28, change "Ml" to --mL--.
At column 16, line 30, change "ml " to --mL--.

Signed and Sealed this

Twelfth Day of October, 1999

Q. TODD DICKINSON

Attest:

Attesting Officer

Acting Commissioner of Patents and Trademarks